(12) United States Patent
Hsieh

(10) Patent No.: US 12,012,400 B2
(45) Date of Patent: Jun. 18, 2024

(54) METHOD OF THE PREPARATION OF FUSED MULTICYCLIC COMPOUNDS

(71) Applicant: National Health Research Institutes, Miaoli County (TW)

(72) Inventor: Hsing-Pang Hsieh, Miaoli County (TW)

(73) Assignee: NATIONAL HEALTH RESEARCH INSTITUTES, Zhunan Town (TW)

( * ) Notice: Subject to any disclaimer, the term of this patent is extended or adjusted under 35 U.S.C. 154(b) by 54 days.

(21) Appl. No.: 17/651,769

(22) Filed: Feb. 18, 2022

(65) Prior Publication Data
US 2023/0265088 A1    Aug. 24, 2023

(51) Int. Cl.
*C07D 417/12*    (2006.01)

(52) U.S. Cl.
CPC ........ *C07D 417/12* (2013.01); *C07B 2200/13* (2013.01)

(58) Field of Classification Search
CPC .................................................... C07D 417/12
USPC ........................................................ 544/284
See application file for complete search history.

(56) References Cited

U.S. PATENT DOCUMENTS 9,006,252 B2    4/2015  Hsieh et al.

OTHER PUBLICATIONS

Julakanti Satyanarayana Reddy et al; "Development of a Robust Scale-Up Synthetic Route for BPR1K871: A Clinical Candidate for the Treatment of Acute Myeloid Leukemia and Solid Tumors" Feb. 18, 2021; Org. Process Res. Dev. 2021, 25, pp. 817-830.

*Primary Examiner* — Kahsay Habte
(74) *Attorney, Agent, or Firm* — Muncy, Geissler, Olds & Lowe, P.C.

(57) ABSTRACT

The present invention discloses a process for preparing compounds of Formula (I), particularly, a process manufacturing thereof on a multikilogram scale:

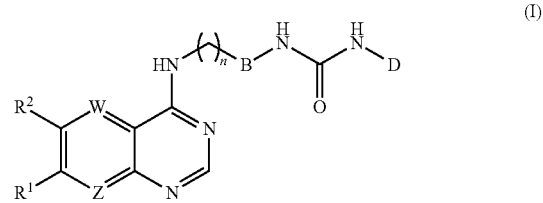

wherein B, D, W, Z, $R^1$, $R^2$, and n are defined herein.

22 Claims, No Drawings

METHOD OF THE PREPARATION OF FUSED MULTICYCLIC COMPOUNDS

BACKGROUND

Kinase inhibitors are a class of targeted anti-cancer drugs that block the overexpressed and/or mutant kinase functions. US FDA (U.S.A. Food and Drug Administration) has approved some inhibitors that target around 20 kinases (Roskoski, *Pharmacol. Res.* 2020, 152, 104609). Additionally, numerous kinase inhibitors are registered in clinical trials and are at different drug development phases (Lightfoot et. al., *ACS Med. Chem. Lett.* 2018, 10, 153-160).

U.S. Pat. No. 9,006,252 discloses a series of quinazoline-based compounds as multi-kinase inhibitors with potent enzymatic and cellular activities in multiple solid tumor cell lines and in vivo efficacy in leukemia, colorectal and pancreatic xenograft mouse models upon intravenous administration. The reported synthetic route consisted of seven steps from commercially available 2-amino-4-fluorobenzoic acid in milligram yields. However, scale-up to gram-scale synthesis resulted in a decrease in yield.

There are also several drawbacks were identified during the scale-up synthesis including: (i) variable yields during the chlorination and $S_NAr$ step and the final dimethyl amination step, increases the overall cost of synthesis, (ii) the use of unsafe reagent NaH/DMF and (iii) the requirement for several column chromatography purifications steps. For pharmaceutical applications, it is necessary to seek an alternative, safe, and efficient route to provide multi-kilograms of these compounds in a high yield with easy to purify steps.

SUMMARY

As discussed above, there remains a need for the development of robust scale-up synthetic route for quinazoline compounds. This invention relates to a process for preparing a compound of Formula (I) or a pharmaceutically acceptable salt thereof, wherein, B is an arylene or heteroarylene; D is an alkyl, alkenyl, alkynyl, aryl, monocyclic heteroaryl, cycloalkyl, cycloalkenyl, heterocycloalkyl, or hetrocycloalkenyl group; W and Z is, independently, N or $CR^a$, $R^a$ being hydrogen, alkyl, alkenyl, alkynyl, aryl, monocyclic heteroaryl, cycloalkyl, cycloalkenyl, heterocycloalkyl, hetrocycloalkenyl alkoxy, halogen, alkoxy amino, or alkoxy alkylamino group; $R^1$ and $R^2$ is, independently, being hydrogen, halogen, or —OA, wherein $R^1$ and $R^2$ are not both hydrogens; A is an alkylamino group; n is 0, 1, 2, 3, or 4; and the process comprising: reacting a compound of Formula (II) with a compound of Formula (III). In some preferred embodiments, the compound of Formula (I) is recrystallized from solvents.

In certain embodiments, the process further comprising: converting a compound of Formula (IV) to the compound of Formula (III). In some preferred embodiments, the compound of Formula (III) is recrystallized from solvents.

In certain embodiments, the process further comprising: reacting a compound of Formula (V) with a compound of Formula (VI) to form a compound of Formula (IV). In some preferred embodiments, the compound of Formula (IV) is provided as solid by centrifugation.

In certain embodiments, the process further comprising: converting a compound of Formula (VII) to the compound of Formula (VI). In some preferred embodiments, the compound of Formula (VI) is provided by removing the compound of Formula (VII) from the mixture thereof using liquid-liquid extraction. In some preferred embodiments, the liquid-liquid extraction is conducted by adding ETOAc to the mixture and collecting the compound of Formula (VI) therein.

In certain embodiments, the process further comprising: reacting a compound of Formula (VIII) with a alkanolamine to form a compound of Formula (VII): wherein X and Y is, independently, being a halogen or hydrogen, X and Y are not both hydrogens. In certain other embodiments, the alkanolamine is a compound of Formula (IX), wherein A is

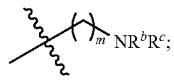

wherein $R^b$ and $R^c$ is, independently, hydrogen, alkyl, alkenyl, alkynyl, aryl, monocyclic heteroaryl, cycloalkyl, cycloalkenyl, heterocycloalkyl, or hetrocycloalkenyl group; m is 2, 3, or 4. In some preferred embodiments, m is 3 and, each $R^b$ and $R^c$ is methyl group. In some other preferred embodiments, the compound of Formula (VII) is provided as solid by centrifugation.

In certain embodiments, the process further comprising: reacting a compound of Formula (X) with formamidine acetate to form a compound of Formula (VIII). In some preferred embodiments, the compound of Formula (VIII) is provided as solid by centrifugation.

In some preferred embodiments, $R^2$ is hydrogen.

In some preferred embodiments, B is phenyl or thiazolyl group. In some other preferred embodiments, B is

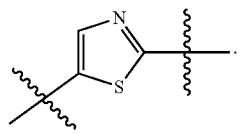 [SMILES: *c1cnc(*)s1]

In some preferred embodiments, D is 6-membered aryl or heteroaryl group. In some other preferred embodiments, D is

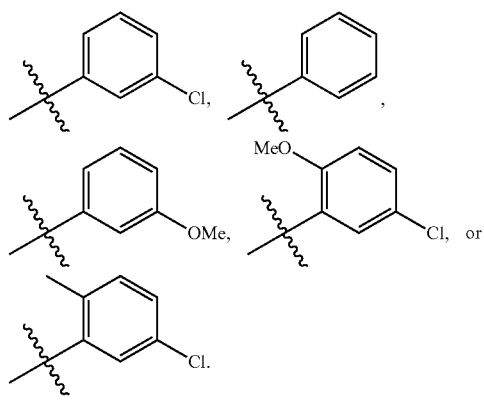

In some preferred embodiments, $R^2$ is hydrogen, A is

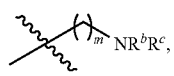

B is

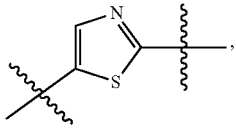 [SMILES: *c1cnc(*)s1],

D is

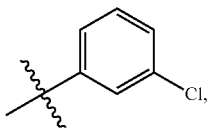

each W, and Z is CR$^a$, R$^a$ is hydrogen, n is 2, m is 3, and each R$^b$ and R$^c$ is methyl group.

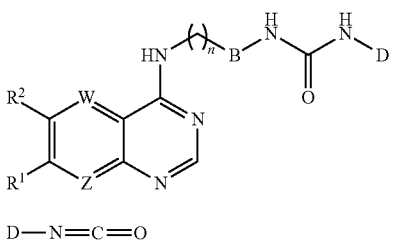 (I)

D—N=C=O (II)

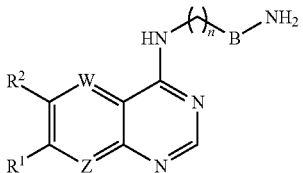 (III)

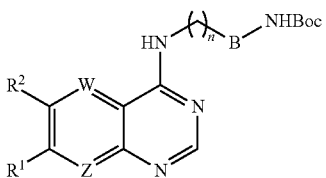 (IV)

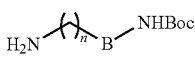 (V)

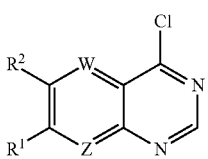 (VI)

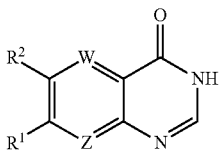 (VII)

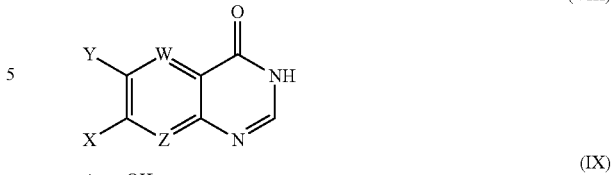 (VIII)

A—OH (IX)

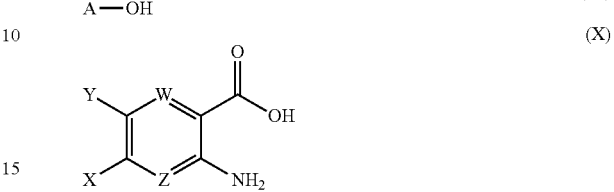 (X)

Definitions

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl", as used herein, refers specifically to cyclic alkyl groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like.

In general, the term "aryl" refers to aromatic moieties, as described above, excluding those attached via an alkyl or heteroalkyl group. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic group, as described above, excluding those attached via an alkyl or heteroalkyl group. In certain embodiments of the present invention, the term "heteroaryl", as used herein, refers to a cyclic unsaturated radical having from about five to about ten ring atoms of which one ring atom is selected from S, O and N, zero, one or two ring atoms are additional heteroatoms independently selected from S, O and N: and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Substituents for aryl and heteroaryl groups include, but are not limited to, any of the previously mentioned substitutents, i.e., the substituents recited for aliphatic moieties, or for other moieties as disclosed herein, resulting in the formation of a stable compound.

The terms alkoxy as used herein refers to an alkyl group, as previously defined, attached to the parent molecular moiety through an oxygen atom. In certain embodiments, the alkyl group contains about $H_2O$ aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups, include but are not limited to, methoxy, ethoxy, propoxy, isopropoxy, n-butoxy, tert-butoxy, neopentoxy and n-hexoxy.

The term "alkylamino" refers to a group having the structure —N(R)$_2$ wherein each occurrence of R is independently hydrogen, or an aliphatic, heteroaliphatic, aromatic or heteroaromatic group, or the R groups, taken together, may form a heterocyclic group.

The terms "halo" and "halogen" as used herein refer to an atom selected from fluorine, chlorine, bromine and iodine.

As used herein, the terms "alkyl", "alkenyl", "alkynyl", "heteroalkyl", "heteroalkenyl", "heteroalkynyl and the like encompass substituted and unsubstituted, saturated and unsaturated, and linear and branched groups. Similarly, the terms heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalknyl", "aromatic", "heteroaromatic", "aryl", "heteroaryl" and the like, used alone or as part of a larger moiety, encompass both substituted and unsubstituted groups.

Compounds of this invention include those generally set forth above and described specifically herein, and are illustrated in part by the various classes, subgenera and species disclosed herein. The details of one or more embodiments of the invention are set forth in the description below. Other features, objects, and advantages of the invention will be apparent from the description and from the claims.

DETAILED DESCRIPTION

Shown below are exemplary compounds of this invention

Compound 1

Compound 2

Compound 3

Compound 4

Compound 5

Compound 6

Compound 7

Compound 8

•3TFA

Compound 9

Compound 10

The previously reported medicinal chemistry synthetic route with seven steps had encountered several issues during scale-up syntheses such as low yields, the formation of inseparable impurities, particularly in the chlorination step, use of hazardous reagents (NaH/DMF) and laborious column chromatography steps for the purification of the products (Hsu, Y. C., et. al. *Oncotarget* 2016, 7, 86239-86256). A step-by-step approach to overcome the above issues was planned in the following examples.

Example 1

Synthesis of the Compound of Formula (VIII) by Condensation with Formamidine

The compound of Formula (VIII) can be obtained by reacting the compound of Formula (X) with formamidine (Scheme 1); wherein W and Z is, independently, N or $CR^a$, $R^a$ being hydrogen, alkyl, alkenyl, alkynyl, aryl, monocyclic heteroaryl, cycloalkyl, cycloalkenyl, heterocycloalkyl, hetrocycloalkenyl alkoxy, halogen, alkoxy amino, or alkoxy alkylamino group; wherein X and Y is, independently, being a halogen or hydrogen, X and Y are not both hydrogens. Preferably, the compound of Formula (VIII) is provided as solid by centrifugation.

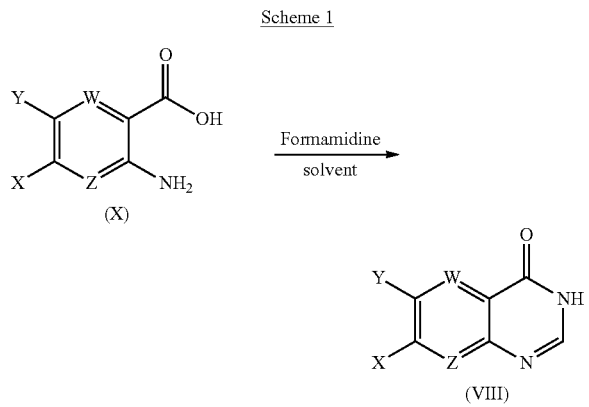

Scheme 1

As an example, the quinazolinone 2 was synthesized from the starting material 1 by condensation with formamidine acetate. The following three conditions were studied to optimize this reaction for a 10.0 g scale of starting material 1 (Table 1). In this reaction system, the resulting product 2 was not soluble in EtOH at room temperature, facilitating the easy isolation of a pure product by simple filtration.

TABLE 1

| Entry | Solvent | Time (h) | Temp (° C.) | 3 Yield (%) |
|---|---|---|---|---|
| 1 | neat | 12 | 120 | 63 |
| 2 | DMSO | 4 | 120 | 83 |
| 3 | EtOH | 40 | reflux | 93 |

The unreacted starting material 1 could be removed successfully in the workup process. Once the reaction is completed, the batch temperature was gradually decreased to about 10-15° C. and stirred for 4 h. The precipitated product vas centrifuged to get the cake, rinsed with cold EtOH, and dried under vacuum at 55° C. for 24 h to afford 2.

7-Fluoroquinazolin-4(3H)-one (2). $^1$H-NMR (400 MHz, DMSO-$d_6$) δ12.35 (brs, 1H), 8.16 (dd, J=8.8, 6.4 Hz, 1H), 8.13 (s, 11H), 7.45 (dd. J=10.4, 2.8 Hz. 1H), 7.39 (ddd, J=8.4, 8.8, 2.4 Hz, 1H). $^{13}$C NMR (100 MHz, DMSO-$d_6$), δ166.8-164.3 (d, J=249.3 Hz), 160.0, 150.9 (d, J=13.0 Hz), 146.8, 128.9 (d, J=10.7 Hz). 119.6, 115.2 (d, J=23.7 Hz), 112.3 (d, J=21.4 Hz). HRMS (ESI) calcd for $C_8H_5FN_2NaO$ [M+Na]: 187.0283; found 187.0283.

Example 2

Formation of the Compound of Formula (VII) by SNAr Attack with Alkanolamine

The compound of Formula (VII) can be obtained by reacting the compound of Formula (VIII) with alkanolamine in basic condition (Scheme 2); w herein W and Z is, independently, N or $CR^a$, $R^a$ being hydrogen, alkyl, alkenyl, alkynyl, aryl, monocyclic heteroaryl, cycloalkyl, cycloalkenyl, heterocycloalkyl, hetrocycloalkenyl alkoxy, halogen, alkoxy amino, or alkoxy alkylamino group: $R^1$ and $R^2$ is, independently, being hydrogen, halogen, or —OA, wherein $R^1$ and $R^2$ are not both hydrogens; A is an alkylamino group; wherein X and Y is, independently, being a halogen or hydrogen, X and Y are not both hydrogens. In some embodiments, the alkanolamine has a Formula (IX). Preferably, the compound of Formula (VII) is provided as solid by centrifugation.

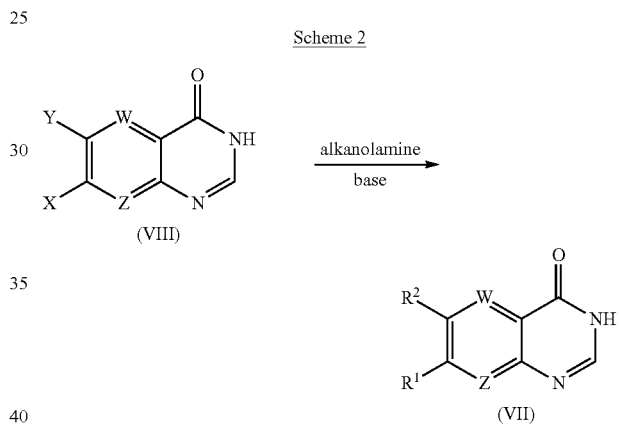

Scheme 2

Take the synthesis of 4 as an example, the reaction conditions were set out to optimize for kilogram-scale synthesis (Table 2). The reaction could be progressed in neat 3-(dimethylamino)propan-1-ol (3) using KOH as the base, the reaction was quenched with water, and then the product 4 isolated by ethyl acetate extraction in good yields (88% isolated yield) in a 10.0 g scale reaction

TABLE 2

| | | | | 4 | |
|---|---|---|---|---|---|
| Entry | 2 (g) | Solvent | Temp (° C.) | Yield (%) | Purity (%) |
| 1 | 10.0 | DMSO | 140 | 55 | 98.5 |
| 2 | 10.0 | DMSO | 125 | 83 | 98.1 |
| 3 | 20.0 | neat | 120 | 73 | 98.4 |
| 4 | 560.0 | neat | 120 | 79 | 99.1 |

Preferably, a special apparatus (Reddy et. al., *Org. Process Res. Dev.* 2021, 25, 817-83(1) was used for the continuous extraction of the aqueous phase for a longer time (3 days) using ethyl acetate or $CH_2Cl_2$. Continuous extraction with EtOAc without adjustment of pH by adding 6 N HCl to the reaction mixture (pH>10) provides the desired product 4 with relatively good yield and purity (after slurry purification disposal).

7-(3-(Dimethylamino)propoxy)quinazolin-4(3H)-one (4). $^1$H-NMR (400 MHz, DMSOd$_6$) δ12.07 (brs, 1H), 8.04 (s, 1H), 8.00 (d, J=9.6 Hz, 1H), 7.08 (t, J=7.6 Hz, 2H), 4.13 (t, J=6.4 Hz, 2H), 2.37 (t, J=6.8 Hz, 2H), 2.15 (s, 6H), 1.91-1.84 (m, 2H). $^{13}$C-NMR (100 MHz, DMSO-d$_6$), δ 163.2, 160.2, 150.9, 145.9, 127.4, 116.3, 115.9, 108.8, 66.3, 55.5, 45.1, 26.6. HRMS (ESI) calcd for C$_{13}$H$_{18}$N$_3$O$_2$ [m+H]: 248.1399; found 248.1395.

Example 3

Production of the Compound of Formula (VI) by Chlorination

The compound of Formula (VI) can be obtained by chlorination of the compound of Formula (VII) (Scheme 3); wherein W and Z is, independently, N or CR$^a$, R$^a$ being hydrogen, alkyl, alkenyl, alkynyl, aryl, monocyclic heteroaryl, cycloalkyl, cycloalkenyl, heterocycloalkyl, hetrocycloalkenyl alkoxy, halogen, alkoxy amino, or alkoxy alkylamino group; R$^1$ and R$^2$ is, independently, being hydrogen, halogen, or —OA, wherein R$^1$ and R$^2$ are not both hydrogens: A is an alkylamino group; n is 0, 1, 2, 3, or 4. Typically, POCl$_3$, SOCl$_2$, Cl$_2$, can be utilized as chloride donor. Preferably, the compound of Formula (VI) is provided by removing the compound of Formula (VII) from the reaction mixture using liquid-liquid extraction. Some alternatives to chlorination include bromination and the introduction of OTf, OSO$_2$CF$_3$, SOPh, SO$_2$Ph, SO$_2$Et or SOEt etc. to set up a good leaving group for following S$_N$Ar reaction.

Scheme 3

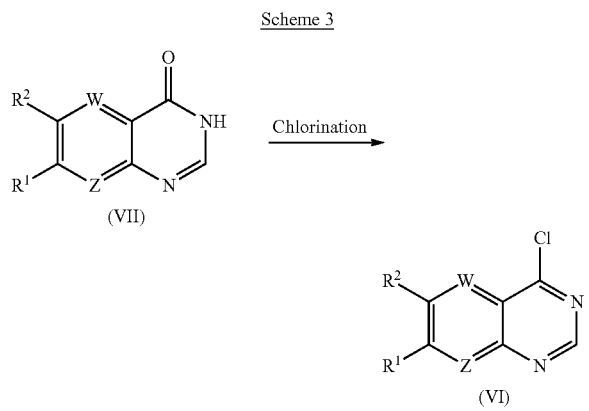

The chlorination reactions with different solvents and reaction conditions were investigated for the efficient production of 5 (Table 3). Completion of the reaction was monitored using HPLC, both by monitoring the disappearance of the reactant 4 and the formation of the product 5. The purity of the product was influenced both by the reaction solvent and reaction's batch size. The crude product 5 was directly used in the next step (S$_N$Ar reaction) after workup, as it was not stable on isolation.

TABLE 3

| Entry | 4 (g) | Temp (° C.) | solvent | Time (h) | HPLC (%) 5 | Impurities |
|---|---|---|---|---|---|---|
| 1 | 0.7 | 70 | toluene | 2.0 | 77.4 | 19.2 |
| 2 | 5.0 | 65 | CH$_3$CN | 2.0 | 93.9 | 2.7 |
| 3 | 20.0 | 65 | CH$_3$CN | 1.5 | 94.1 | 3.0 |

TABLE 3-continued

| Entry | 4 (g) | Temp (° C.) | solvent | Time (h) | HPLC (%) 5 | Impurities |
|---|---|---|---|---|---|---|
| 4 | 108.0 | 70 | CH$_3$CN | 1.5 | 90.2 | 5.4 |
| 5 | 164.0 | 80 | CH$_3$CN | 8.0 | 96.7 | 2.1 |

Example 4

Preparation of the Compound of Formula (IV) by S$_N$Ar Reaction

A compound of Formula (IV) can be obtained by S$_N$Ar reaction of the compound of Formula (VI) with a compound of Formula (V) (Scheme 4); wherein B is an arylene or heteroarylene; W and Z is, independently, N or CR$^a$, R$^a$ being hydrogen, alkyl, alkenyl, alkynyl, aryl, monocyclic heteroaryl, cycloalkyl, cycloalkenyl, heterocycloalkyl, hetrocycloalkenyl alkoxy, halogen, alkoxy amino, or alkoxy alkylamino group: R$^1$ and R$^2$ is, independently, being hydrogen, halogen, or —OA, wherein R$^1$ and R$^2$ are not both hydrogens; A is an alkylamino group; n is 0, 1, 2, 3, or 4. Preferably, the compound of Formula (IV) is provided as solid by centrifugation.

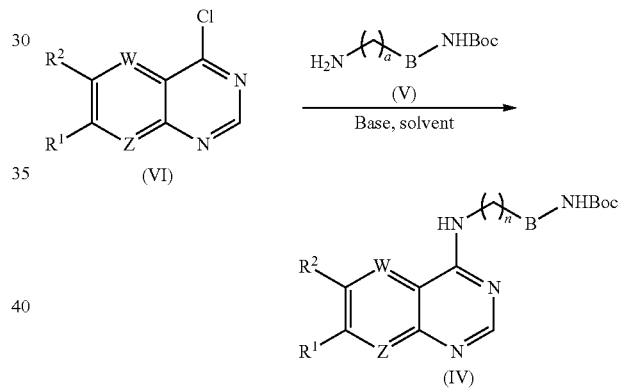

Different types of bases and solvent conditions were tested for the S$_N$Ar displacement reaction of 5 with 6 (Table 4). There was a need to remove the ~3% level of impurity present in the final product. The use of a mixture of EtOAc/MeOH (10:1.5) solvent to wash the product 7 removed the impurity successfully.

TABLE 4

| Entry | 5 (g) | base | solvent | Temp (° C.) | Time (h) | HPLC (%) 7 | Impurities |
|---|---|---|---|---|---|---|---|
| 1 | 0.60 | Et$_3$N | i-PrOH | 80 | 2.5 | 83.0 | 8.9 |
| 2 | 0.60 | Et$_3$N | EtOH | 80 | 2.5 | 83.3 | 8.0 |
| 3 | 5.00 | K$_2$CO$_3$ | DMF | 70 | 2.0 | 72.4 | 9.7 |
| 4 | 3.30 | K$_2$CO$_3$ | DMAC | 70 | 2.5 | 75.1 | 12.2 |
| 5 | 3.34 | DIPEA | i-PrOH | 80 | 3.0 | 79.1 | 11.3 |
| 6 | 0.50 | DIPEA | EtOH | 80 | 2.0 | 68.3 | 16.5 |
| 7 | 1.20 | DIPEA | CH$_3$CN | 65 | 7.0 | 96.4 | 3.5 |
| 8 | 517.30 | DIPEA | CH$_3$CN | 65 | 9.0 | 95.0 | 3.3 | tert-Butyl(5-(2-((7-(3-(dimethylamino)propoxy)-quinazolin-4-yl)amino)ethyl)thiazol-2-yl) Carbamate (7) $^1$H-NMR (400 MHz, DMSO-d$_6$) δ11.16 (brs, 2H), 8.41 (s, 1H), 8.24 (t, J=5.2 Hz, 1H), 8, 1 (d, J=9.2 Hz 1H), 7.11 (dd, J=9.2, 2.4 Hz, 2H), 7.07 (dd, J=8.4, 2.4 Hz. 2H), 4.12 (t, J=6.4 Hz, 2H), 3.70 (q, J=12.8, 6.8 Hz, 2H), 3.06 (t, J=6.8 Hz, 2H), 2.38 (t, J=7.2 Hz, 2H), 2.15 (s, 6H), 1.92-1.85 (m, 2H), 1.44 (s, 9H). $^{13}$C-NMR (100 MHz, DMSO-d$_6$) δ161.7, 158.9, 158.3, 155.5, 152.7, 151.3, 134.9, 128.3, 124.2, 116.9, 109.1, 107.4, 80.8, 66.1, 55.5, 45.1, 41.7, 27.8, 26.6, 25.7 HRMS (ESI) calcd for $C_{23}H_{32}N_6NaO_3S$ [M+Na]: 495.2154; found 495.2679.

Example 5

Removing Boc Group to Obtain the Compound of Formula (II)

The compound of Formula (II) can be obtained by removing the Boc protective group from a compound of Formula (IV) in acidic condition (Scheme 5); wherein B is an arylene or heteroarylene; W and Z is, Independently, N or CR$^a$, R$^a$ being hydrogen, alkyl, alkenyl, alkynyl, aryl, monocyclic heteroaryl, cycloalkyl, cycloalkenyl, heterocycloalkyl, hetrocycloalkenyl alkoxy, halogen, alkoxy amino, or alkoxy alkylamino group: R$^1$ and R$^2$ is, independently, being hydrogen, halogen, or —OA, wherein R$^1$ and R$^2$ are not both hydrogens: A is an alkylamino group; n is 0, 1, 2, 3, or 4. Preferably, the compound of Formula (II) is recrystallized from solvents.

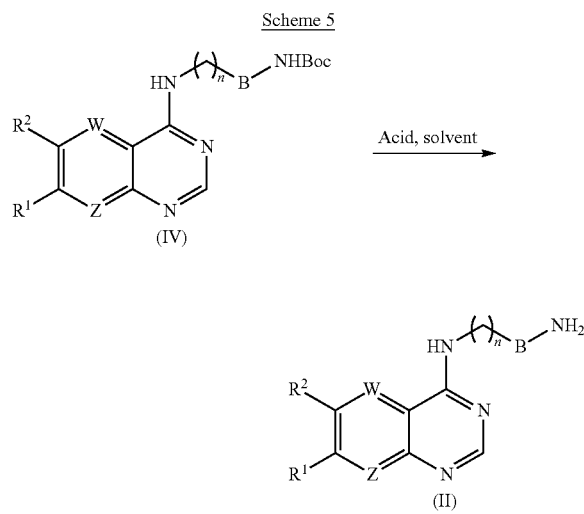

The synthesis of intermediate 8 was taken as an example. To obtain high purity on a bulk scale, compound 7 was reacted with TFA in dichloromethane at around 40-45° C. to remove the Boc protective group to get 8 as TFA salt. The pure product's isolation from the reaction mixture required a robust recrystallization procedure, for which MTBE (methyl tert-butyl ether) and MeOH solvent mixture was used. Consequently, using the above reaction and workup method, intermediate 8 was obtained in an excellent yield (99%) and HPLC purity (98.2%) without the need for column purification.

5-(2-((7-(3-(Dimethylamino)propoxy)quinazolin-4-yl) amino)ethyl)thiazol-2-amine (8), $^1$HNMR (400 MHz, DMSO-d$_6$) δ9.98 (brs, 1H). 9.83 (brs, 1H), 8.86 (s, 1H), 8.69 (s, 1H), 8.38 (d, J=9.6 Hz. 1H), 7.40 (dd. J=9.2, 2.4 Hz, 1H), 7.25 (d, J=2.4 Hz, 1H), 7.04 (s, 1H), 4.24 (t, J=6.0 Hz, 2H), 3.86 (q, J=12.4, 6.4 Hz, 2H), 3.25 (brs, 2H), 3.03 (t, J=6.4 Hz 2H), 2.83 (s, 6H), 2.22-2.15 (m, 2H)$^{13}$C-NMR (100 MHz, DMSO-d$_6$) δ169.6, 163.6, 160.1, 158.9 (q, J=64.9, 32.8 Hz, C═O, trifluoroacetic acid), 151.4, 140.2, 125.7 (d, J=98.4 Hz), 121.4 (CF$_3$, trifluoroacetic acid), 118.4 (d, J=31.3 Hz), 115.3, 106.9, 101.2, 65.9, 53.9, 42.2, 41.8, 25.5, 23.6. HRMS (ESI) calcd for $C_{18}H_{25}N_6OS$ [M+H]: 373.1810; found 373.1807.

Example 6

Urea Bond Formation to Provide the Compound of Formula (I)

The compound of Formula (I) can be obtained by reacting a compound of Formula (III) with a compound of Formula (II) in basic condition (Scheme 6); wherein B is an arylene or heteroarylene, D is an alkyl, alkenyl, alkynl, aryl, monocyclic heteroaryl, cycloalkyl, cycloalkenyl, heterocycloalkyl, or hetrocycloalkenyl group; W and Z is, independently. N or CR$^a$, R$^a$ being hydrogen, alkyl, alkenyl, alkynyl, aryl, monocyclic heteroaryl, cycloalkyl, cycloalkenyl, heterocycloalkyl, hetrocycloalkenyl alkoxy, halogen, alkoxy amino, or alkoxy alkylamino group; R$^1$ and R$^2$ is, independently, being hydrogen, halogen or —OA, wherein R$^1$ and R$^2$ are not both hydrogens, A is an alkylamino group; n is 0, 1, 2, 3, or 4 Preferably, the compound of Formula (I) is recrystallized from solvents.

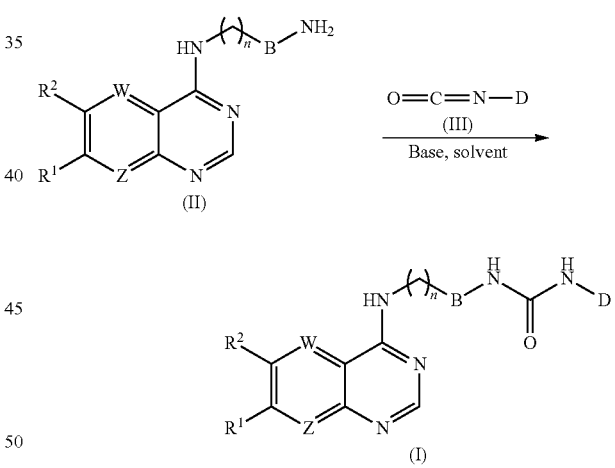

As an example, the compound 10 was synthesized using the coupling reaction, where the reaction between intermediate 8 and 3-chlorophenyl isocyanate (9) was carried out in DCM using Et$_3$N as a base Solvent systems were screening to carry out the urea bond formation (Table 5). The reaction in CH$_2$Cl$_2$/CH$_3$CN (1:1) solvent mixture went on to completion with a good yield of the compound 10, which was isolated by recrystallization from a mixture of CH$_3$CN and MeOH (1:1). The CH$_2$Cl$_2$/CH$_3$CN (1.1) solvent system avoided sticky gel formation during the reaction process. Moreover, it was found that the starting material's moisture content needs to be kept at a minimum so that 8 could be consumed completely during the reaction to get the compound 10 in high purity.

TABLE 5

| Entry | 8 (g) Solvent | Time (h) | Yield (%) | Purity (%) |
|---|---|---|---|---|
| 1 | 10.0 $CH_2Cl_2$ | 12 | 65.2 | 89.4 |
| 2 | 10.0 $CH_2Cl_2$/MeOH | 12 | 66.0 | 96.5 |
| 3 | 16.6 $CH_2Cl_2$/$CH_3CN$ | 5 | 69.3 | 96.9 |
| 4 | 130.0 $CH_2Cl_2$/$CH_3CN$ | 5 | 92.9 | 97.7 |

1-(3-Chlorophenyl)-3-(5-(2-((7-(3-(dimethylamino)propoxy)quinazolin-4-yl)amino)ethyl)thiazol-2-yl)urea (10). $^1$H-NMR (400 MHz, DMSO-$d_6$) δ 10.64 (brs, 1H), 9.20 (brs, 1H), 8.41 (s, 1H), 8.25 (t, J=5.6 Hz, 1H), 8.11 (d, J=9.2 Hz, 1H), 7.70 (s, 1H), 7.33-7.28 (m, 2H), 7.11 (dd, J=9.2, 3.2 Hz, 2H), 7.05 (m, 2H), 4.12 (t, J=6.4 Hz, 2H), 3.72 (q, J=12.8, 6.8 Hz. 2H), 3.07 (t, J=7.2 Hz, 2H), 2.38 (t, J=7.2 Hz, 2H), 2.15 (s, 6H), 1.92-1.85 (n. 21-1). $^{13}$C-NMR (100 MHz, DMSO-$d_6$) δ 161.7, 159.2, 158.9, 155.6, 152.5, 151.3, 140.5, 133.2, 132.7, 130.4, 127.3, 124.2, 122.0, 117.8, 116.9, 109.1, 107.4, 66.0, 55.5, 45.1, 41.6, 26.6, 25.8. HRMS (ESI) calcd for $C_{25}H_{28}ClN_7NaO_2S$ [M+Na]: 548.1611; found 548.1598.

Example 7

Kilogram-Scale Total Synthesis of the Compound of Formula (I)

Herein, it is demonstrated a practical and scale-up procedure that can operate on a 3 kg scale for the production of compound 10. The optimized process manufacturing was run on a multikilogram scale in a kilo lab facility using a six-step reaction sequence. All the steps provided the product as solid and were centrifugation either from the reaction mixture directly or recrystallized from solvents to get the product in high purity.

A 200.0 L glass-lined jacketed reactor was charged with ethanol (70.0 kg) and 2-amino-4-fluorobenzoic acid (1) (9.70 Kg, 62.52 mol. 1.0 equiv). The resulting mixture was stirred at room temperature and then added formamidine acetate (13.13 kg. 125.04 mol, 2.0 equiv) in one portion at the same temperature. The reaction mixture was warmed to reflux and stirred for 2 days. When the HPLC analysis indicated <4% of the starting material 1 remained, the batch temperature was gradually decreased to 10-15° C. and stirred for 4 h at that temperature. While maintaining the internal temperature of 10-15° C. the compound was precipitated, the mixture was centrifuged, and the cake was rinsed with ethanol (8.0 Kg). The wet cake was dried in an oven under vacuum at 55° C. for 24 h to afford compound 2 (9.17 kg. 89.4%) as an off-white solid with an HPLC purity of 99.8%.

Another 200.0 L glass-lined jacketed reactor was charged with 3-(dimethylamino)propan-1-ol (3) (31.62 kg. 306.59 mol, 5.5 equiv) and powdered KOH (12.51 kg. 222.98 mol, 4.0 equiv). The resulting mixture was warmed to 120° C. and stirred for 1 h. Then, quinazolinone 2 (9.15 kg, 55.75 mol, 1.0 equiv) was added to the reactor at that temperature. The reaction mixture was stirred at the same temperature for 8 h; HPLC analysis indicated only 0.3% of 2 remained (Rt=6.9 min). The reaction mixture was cooled down to 15° C., and $H_2O$ (100.0 L) was added to the reactor dropwise over a 1 h period while maintaining the internal temperature at 20-25° C. The resulting mixture was continuously extracted with EtOAc (650.0 kg) for 3 days using a liquid-liquid continuous extractor (Reddy et. al. *Org. Process Res. Dev.* 2021, 25, 817-83(1). Finally, the aqueous phase was extracted twice with a mixture of EtOAc (150.0 kg 2) and EtOH (10.0 kg/2); the combined organic phase was concentrated under vacuum at 50° C. until the volume was about 55.0 L. The mixture was treated with EtOH (5.0 kg) and heated to 45° C. for 1 h. The solution temperature was decreased to 15° C. and held for about 2 h to afford the product's precipitation. The mixture was centrifuged, collected the solid, and the cake rinsed with a mixture of EtOAc (4.9 kg) and EtOH (0.46 kg), which gave 11.20 kg wet cake. The wet cake was dried in an oven under vacuum at 45° C. for 18 h to give the desired product 4 (9.22 kg. 66.9%) as a white solid, with an HPLC purity of 98.5%.

A 50.0 L glass-lined jacketed reactor was charged with $CH_3CN$ (7.8 kg) and 4 (1.64 kg. 6.63 mol. 1.0 equiv) and stirred at room temperature. Further, $POCl_3$ (2.03 kg. 13.26 mol, 2.0 equiv) was added into the reaction mixture over 10 min while maintaining the batch temperature below 30° C. The temperature was increased to ~80° C. over 45 min (the reaction mixture cleared at 56° C.) and held for 8 h. The completion of the reaction was established by HPLC analysis, which indicated that the unreacted starting material was around 1%. The reaction was cooled to ~35° C. over 1 h. charged with $CH_2Cl_2$ (46.0 kg), and then transferred into a dropping tank. The mixture in the dropping tank was transferred into a 12.5% $K_2HPO_4$ aqueous quench solution (97.4 kg) in a 200.0 L reactor over a 20 min period while maintaining the temperature −5 to +5° C. to reach the target pH 4-5 Then, 50% $K_2CO_3$ aqueous solution (14.8 kg) was charged into the reactor over 20 min at 5-15° C. until pH 9-10. The mixture was stirred for 20 min at about 15° C. and settled to split layers. The organic layer was separated, and the aqueous layer was washed with $CH_2Cl_2$ (46.0 kg) again. The combined organic phase was washed with 5% brine (33.0 kg) and dried over $Na_2SO_4$ (6.6 kg) for 2 h. The mixture was filtered and rinsed with $CH_2Cl_2$ (13.0 kg), the filtrate was sampled for HPLC purity and found to be 96.7%. Due to the instability of chloro compound 5, the above filtrate was directly used for the next step.

The amine 6 (1.45 kg, 5.97 mol, 0.9 equiv) was directly charged into the filtrate 5, which was obtained in the earlier step. The reaction mixture was then concentrated under vacuum at 20° C. to about 2.5 L volume and was charged with $CH_3CN$ (4.2 kg) and then concentrated to about 4.1 L volume. The mixture was transferred to a 50.0 L reactor, and $CH_3CN$ (6.6 kg) and DIPEA (0.856 kg. 6.63 mol. 1.0 equiv) were charged into the reactor. The mixture was heated to 55° C. and held for 2 h; then the batch temperature raised to 65° C. over 30 min and held for 2 h with stirring. An additional amount of amine 6 (0.161 kg. 0.663 mol, 0.1) was charged into the reactor at that temperature. The reaction temperature was raised to 75° C. and stirred for 4 h. The reaction mixture was sampled by HPLC, which detected 3.5% unreacted starting material 5. Then. MeOH (0.62 L) was added into the reactor while the temperature was maintained at about 65° C. and held for 1 h. The mixture was cooled to 20° C. over 2 h. The mixture was stirred for about 5 h and then centrifuged to get the crude cake and washed with a mixture of $CH_3CN$ (7.0 kg) and MeOH (0.40 kg) to get 4.56 kg 7 as a wet-cake with 89.5% HPLC purity. A solution of EtOAc (6.32 kg) and MeOH (1.26 kg) and the wet cake 4.56 kg in a 50 L reactor was heated to 85° C. for 12 h. Then, the reaction temperature cooled to 20° C. over 2.5 h and held for 3 h. The mixture was centrifuged, and the cake was rinsed with EtOAc (4.0 kg) to afford a 1.30 kg product. The wet cake was dried in an oven under vacuum at 50° C. for 10 h to get the product 7 (1.22 kg. 38.9% yield over two steps) as a light brown solid with 96.8% HPLC purity.

A 100.0 L jacketed reactor was flushed with nitrogen and charged with Boc-amine 7 (4.00 kg. 8.46 mol. 1.0 equiv) and CH$_2$Cl$_2$ (42.2 kg). Trifluoroacetic acid (15.20 kg, 132.88 mol, 15.7 equiv) was dropwise added into the reactor over a period of 1 h. while the reaction temperature was maintained <30° C. The resultant mixture w as heated to 45° C. and stirred at that temperature for about 6 h. When the HPLC analysis indicated that <1% of 7 remained, then, the reaction was concentrated to about 10.0 L volume. Subsequently. MeOH (3.2 kg) and MTBE (12.0 kg) were charged into the reactor and stirred at room temperature for about 6 h. The mixture was filtered, and the solid obtained was washed with MTBE (12.0 kg). The wet cake was dried in a vacuum oven at 50° C. for about 2 days to yield 5.85 kg (~99%) of 8 as a white solid with 98.2% HPLC purity.

A 200.0 L jacketed reactor flushed with nitrogen was charged with 8 (5.57 kg. 8.05 mol. 1.0 equiv), CH$_2$Cl$_2$ (61.0 kg), and dry CH$_3$CN (36.8 kg) while stirring at 32° C. Then. Et$_3$N (2.80 kg, 27.63 mol, 3.43 equiv) was added at that temperature over 15 min and stirred for 10 min. Next, 3-chlorophenyl isocyanate (2.06 kg, 13.44 mol, 1.67 equiv) w as added at that temperature over 5 min, and the mixture was stirred for about 4 h while the temperature was maintained at about 35° C.; HPLC analysis determined that <0.07% of the starting material 8 remained unreacted. The reaction was cooled to 25° C. held for 1 h, and then centrifuged to obtain the product as a cake, which was recrystallized with a CH$_3$CN (46.0 kg) and MeOH (36.8 kg) solvent mixture. The wet cake was dried in an oven under vacuum at 50° C. for over 12 h to afford the final product 10 (3.04 kg, 71.8%) as a white solid with purity of 97.8% and 97.2% assay purity with a single maximum impurity of ~0.6-0.7%.

While a number of embodiments of this invention have be described, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The invention claimed is:

1. A process for preparing a compound of Formula (I) or a pharmaceutically acceptable salt thereof,

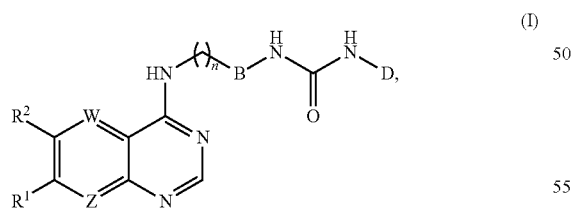

(I)

wherein
B is an arylene or heteroarylene;
D is an alkyl, alkenyl, alkynyl, aryl, monocyclic heteroaryl, cycloalkyl, cycloalkenyl, heterocycloalkyl, hetrocycloalkenyl, chloro-substituted phenyl, methoxy-substituted phenyl, methoxy- and chloro-substituted phenyl, or methyl- and chloro-substituted phenyl group;
W and Z are both CR$^a$, R$^a$ being hydrogen, alkyl, alkenyl, alkynyl, aryl, monocyclic heteroaryl, cycloalkyl, cycloalkenyl, heterocycloalkyl, hetrocycloalkenyl alkoxy, halogen, alkoxy amino, or alkoxy alkylamino group;
R$^1$ and R$^2$ is, independently, being hydrogen, halogen, or

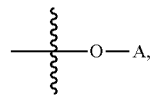

wherein R$^1$ and R$^2$ are not both hydrogens;
A is an alkylamino group;
n is 0, 1, 2, 3, or 4; and
the process comprising:
reacting a compound of Formula (II) with a compound of Formula (III) under basic condition to form a urea bond,

(II)

(III)

2. The process of claim 1, further comprising:
converting a compound of Formula (IV) to the compound of Formula (III),

(IV)

3. The process of claim 2, further comprising: reacting a compound of Formula (V) with a compound of Formula (VI) to form a compound of Formula (IV),

(V)

(VI)

4. The process of claim 3, further comprising:

converting a compound of Formula (VII) to the compound of Formula (VI),

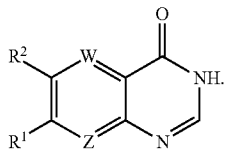
(VII)

5. The process of claim 4, further comprising:

reacting a compound of Formula (VIII) with a alkanolamine to form the compound of Formula (VII); wherein X and Y is, independently, being a halogen or hydrogen, X and Y are not both hydrogens,

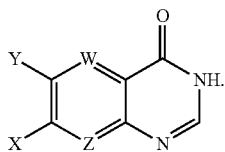
(VIII)

6. The process of claim 5, wherein the alkanolamine is a compound of Formula (IX),

A-OH    (IX).

7. The process of claim 5, further comprising:

reacting a compound of Formula (X) with formamidine acetate to form the compound of Formula (VIII),

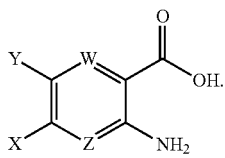
(X)

8. The process of claim 6, wherein A is

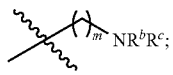

wherein $R^b$ and $R^c$ is, independently, hydrogen, alkyl, alkenyl, alkynyl, aryl, monocyclic heteroaryl, cycloalkyl, cycloalkenyl, heterocycloalkyl, or hetrocycloalkenyl group; m is 2, 3, or 4.

9. The process of claim 8, wherein m is 3 and, each $R^b$ and $R^c$ is methyl group.

10. The process of claim 1, wherein $R^2$ is hydrogen.

11. The process of claim 1, wherein B is phenyl or thiazolyl group.

12. The process of claim 11, wherein B is

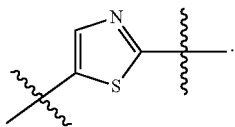 [SMILES: *c1cnc(*)s1]

13. The process of claim 1, wherein D is 6-membered aryl or heteroaryl group.

14. The process of claim 13, wherein D is

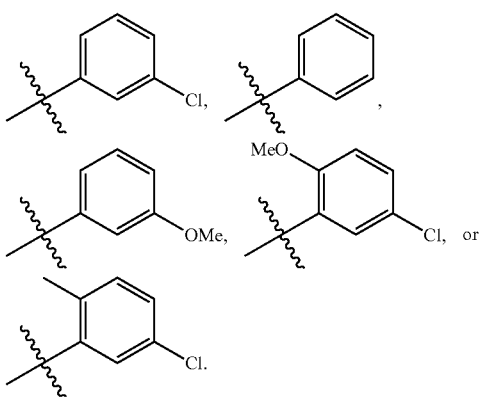

15. The process of claim 1, wherein $R^2$ is hydrogen, A is

B is

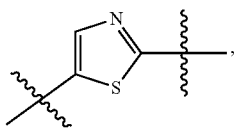

D is

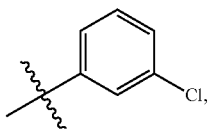

each W and Z is $CR^a$, $R^a$ is hydrogen, n is 2, m is 3, and each $R^b$ and $R^c$ is methyl group.

16. The process of claim 1, wherein the compound of Formula (I) is recrystallized from solvents.

17. The process of claim 2, wherein the compound of Formula (III) is recrystallized from solvents.

18. The process of claim 3, wherein the compound of Formula (IV) is provided as solid by centrifugation.

19. The process of claim 4, wherein the compound of Formula (VI) is provided by removing the compound of Formula (VII) from a mixture thereof using liquid-liquid extraction.

20. The process of claim 19, wherein the liquid-liquid extraction is conducted by adding ETOAc to the mixture and collecting the compound of Formula (VI) therein.

21. The process of claim 5, wherein the compound of Formula (VII) is provided as solid by centrifugation.

22. The process of claim 7, wherein the compound of Formula (VIII) is provided as solid by centrifugation.

* * * * *